(12) United States Patent
Kuntz

(10) Patent No.: US 9,119,639 B2
(45) Date of Patent: Sep. 1, 2015

(54) ARTICULATED CAVITY CREATOR

(75) Inventor: Kyle Kuntz, Malvern, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 61 days.

(21) Appl. No.: 13/205,826

(22) Filed: Aug. 9, 2011

(65) Prior Publication Data
US 2013/0041377 A1 Feb. 14, 2013

(51) Int. Cl.
*A61B 17/32* (2006.01)
*A61B 1/008* (2006.01)
*A61B 17/16* (2006.01)

(52) U.S. Cl.
CPC ........... *A61B 17/1631* (2013.01); *A61B 17/162* (2013.01); *A61B 17/1671* (2013.01)

(58) Field of Classification Search
USPC ............................................. 604/95.04, 528
See application file for complete search history.

(56) References Cited

U.S. PATENT DOCUMENTS

| | | |
|---|---|---|
| 3,223,083 A | 12/1965 | Cobey |
| 3,503,385 A | 3/1970 | Stevens |
| 4,405,249 A | 9/1983 | Scales |
| 4,627,434 A | 12/1986 | Murray |
| 4,630,616 A | 12/1986 | Tretinyak |
| 4,653,489 A | 3/1987 | Tronzo |
| 4,969,888 A | 11/1990 | Scholten et al. |
| 4,998,923 A | 3/1991 | Samson et al. |
| 5,002,543 A | 3/1991 | Bradshaw et al. |
| 5,030,201 A | 7/1991 | Palestrant |
| 5,108,404 A | 4/1992 | Scholten et al. |
| 5,231,989 A | 8/1993 | Middleman et al. |
| 5,284,128 A | 2/1994 | Hart |
| 5,438,975 A * | 8/1995 | Miyagi et al. ................. 600/109 |
| 5,509,923 A | 4/1996 | Middleman et al. |
| 5,512,037 A | 4/1996 | Russell et al. |
| 5,545,200 A | 8/1996 | West et al. |
| 5,709,697 A | 1/1998 | Ratcliff et al. |
| 5,749,879 A | 5/1998 | Middleman et al. |
| 5,755,731 A | 5/1998 | Grinberg |
| 5,851,208 A * | 12/1998 | Trott ............................... 606/80 |
| 5,860,995 A | 1/1999 | Berkelaar |
| 5,904,690 A | 5/1999 | Middleman et al. |
| 5,972,015 A | 10/1999 | Scribner et al. |

(Continued)

FOREIGN PATENT DOCUMENTS

| | | |
|---|---|---|
| WO | 96/13297 | 5/1996 |
| WO | 96/20752 | 7/1996 |

(Continued)

OTHER PUBLICATIONS

European Search Report from application No. 14150828.3-1506, dated Apr. 25, 2014.

*Primary Examiner* — Todd Manahan
*Assistant Examiner* — Eric S Gibson
(74) *Attorney, Agent, or Firm* — Meunier Carlin & Curfman LLC

(57) ABSTRACT

Disclosed herein are devices for use through a cannula to create cavities within interior body regions. When deployed, the distal end of several such devices extend beyond the distal end of the catheter and can then be selectively curved into a shaped compression surface that, when articulated, creates a void within the interior body. This compression surface may then be withdrawn back into the cannula for removal and to make way for bone cement that, in certain instances, may be introduced through the same cannula.

15 Claims, 11 Drawing Sheets

(56) References Cited

U.S. PATENT DOCUMENTS

| | | |
|---|---|---|
| 5,987,344 A | 11/1999 | West |
| 6,019,776 A | 2/2000 | Preissman et al. |
| 6,033,411 A | 3/2000 | Preissman |
| 6,048,339 A | 4/2000 | Zirps et al. |
| 6,048,346 A | 4/2000 | Reiley et al. |
| 6,053,922 A | 4/2000 | Krause et al. |
| 6,099,514 A | 8/2000 | Sharkey et al. |
| 6,217,581 B1 | 4/2001 | Tolson |
| 6,241,734 B1 | 6/2001 | Scribner et al. |
| 6,248,110 B1 | 6/2001 | Reiley et al. |
| 6,280,456 B1 | 8/2001 | Scribner et al. |
| 6,337,142 B2 | 1/2002 | Harder et al. |
| 6,348,055 B1 | 2/2002 | Preissman |
| 6,375,659 B1 | 4/2002 | Erbe et al. |
| 6,383,190 B1 | 5/2002 | Preissman |
| 6,395,007 B1 | 5/2002 | Bhatnagar et al. |
| 6,402,758 B1 | 6/2002 | Tolson |
| 6,440,138 B1 | 8/2002 | Reiley et al. |
| 6,582,446 B1 | 6/2003 | Marchosky |
| 6,613,054 B2 | 9/2003 | Scribner et al. |
| 6,641,587 B2 | 11/2003 | Scribner et al. |
| 6,645,213 B2 | 11/2003 | Sand et al. |
| 6,676,664 B1 | 1/2004 | Al-Assir |
| 6,679,886 B2 | 1/2004 | Weikel et al. |
| 6,716,216 B1 | 4/2004 | Boucher et al. |
| 6,719,761 B1 | 4/2004 | Reiley et al. |
| 6,726,691 B2 | 4/2004 | Osorio et al. |
| 6,730,095 B2 | 5/2004 | Olson, Jr. et al. |
| 6,740,093 B2 | 5/2004 | Hochschuler et al. |
| 6,746,451 B2 | 6/2004 | Middleton et al. |
| 6,770,079 B2 | 8/2004 | Bhatnagar et al. |
| 6,783,515 B1 | 8/2004 | Miller et al. |
| 6,814,736 B2 | 11/2004 | Reiley et al. |
| 6,863,672 B2 | 3/2005 | Reiley et al. |
| 6,875,219 B2 | 4/2005 | Arramon et al. |
| 6,887,246 B2 | 5/2005 | Bhatnagar et al. |
| 6,923,813 B2 | 8/2005 | Phillips et al. |
| 7,048,743 B2 | 5/2006 | Miller et al. |
| 7,066,942 B2 | 6/2006 | Treace |
| 7,153,306 B2 | 12/2006 | Ralph et al. |
| 7,153,307 B2 | 12/2006 | Scribner et al. |
| 7,252,671 B2 | 8/2007 | Scribner et al. |
| 7,264,622 B2 | 9/2007 | Michelson et al. |
| 7,476,226 B2 | 1/2009 | Weikel et al. |
| 7,503,920 B2 | 3/2009 | Siegal |
| 7,544,196 B2 | 6/2009 | Bagga et al. |
| 7,559,932 B2 | 7/2009 | Truckai et al. |
| 7,572,263 B2 | 8/2009 | Preissman |
| 7,585,300 B2 | 9/2009 | Cha |
| 7,591,822 B2 | 9/2009 | Olson, Jr. et al. |
| 7,641,664 B2 | 1/2010 | Pagano |
| 7,666,205 B2 | 2/2010 | Weikel et al. |
| 7,704,256 B2 | 4/2010 | Sand et al. |
| 7,713,273 B2 | 5/2010 | Krueger et al. |
| 7,731,720 B2 | 6/2010 | Sand et al. |
| 7,842,041 B2 | 11/2010 | Liu et al. |
| 7,879,038 B2 | 2/2011 | Reiley et al. |
| 7,909,827 B2 | 3/2011 | Reiley et al. |
| 8,080,061 B2 | 12/2011 | Appenzeller et al. |
| 8,157,806 B2 | 4/2012 | Frigg et al. |
| 2001/0049531 A1 | 12/2001 | Reiley et al. |
| 2002/0026197 A1 | 2/2002 | Foley et al. |
| 2002/0082605 A1 | 6/2002 | Reiley et al. |
| 2002/0151927 A1 | 10/2002 | Douk et al. |
| 2002/0188299 A1 | 12/2002 | Reiley et al. |
| 2002/0188300 A1 | 12/2002 | Arramon et al. |
| 2003/0004537 A1 | 1/2003 | Boyle et al. |
| 2003/0036763 A1 | 2/2003 | Bhatnagar et al. |
| 2003/0163085 A1 | 8/2003 | Tanner et al. |
| 2003/0187445 A1 | 10/2003 | Keith et al. |
| 2003/0187449 A1 | 10/2003 | McCleary et al. |
| 2003/0191474 A1 | 10/2003 | Cragg et al. |
| 2004/0024409 A1 | 2/2004 | Sand et al. |
| 2004/0024410 A1 | 2/2004 | Olson, Jr. et al. |
| 2004/0267269 A1 | 12/2004 | Middleton et al. |
| 2005/0070912 A1 | 3/2005 | Voellmicke |
| 2005/0070913 A1 | 3/2005 | Milbocker et al. |
| 2005/0228397 A1 | 10/2005 | Malandain et al. |
| 2005/0272978 A1 * | 12/2005 | Brunnen et al. .............. 600/142 |
| 2006/0100640 A1 | 5/2006 | Bolduc |
| 2006/0116689 A1 | 6/2006 | Albans et al. |
| 2006/0116690 A1 | 6/2006 | Pagano |
| 2006/0142694 A1 | 6/2006 | Bednarek et al. |
| 2006/0167416 A1 | 7/2006 | Mathis et al. |
| 2007/0043430 A1 | 2/2007 | Stinson |
| 2007/0055279 A1 | 3/2007 | Sand et al. |
| 2007/0055284 A1 | 3/2007 | Osorio et al. |
| 2007/0055285 A1 | 3/2007 | Osorio et al. |
| 2007/0118142 A1 | 5/2007 | Krueger et al. |
| 2007/0118143 A1 | 5/2007 | Ralph et al. |
| 2007/0142842 A1 | 6/2007 | Krueger et al. |
| 2007/0179340 A1 | 8/2007 | Jorgensen |
| 2007/0198020 A1 | 8/2007 | Reiley et al. |
| 2007/0198023 A1 | 8/2007 | Sand et al. |
| 2008/0058827 A1 | 3/2008 | Osorio et al. |
| 2008/0065020 A1 | 3/2008 | Ralph et al. |
| 2008/0065087 A1 | 3/2008 | Osorio et al. |
| 2008/0065190 A1 | 3/2008 | Osorio et al. |
| 2008/0086142 A1 | 4/2008 | Kohm et al. |
| 2008/0091170 A1 * | 4/2008 | Vargas et al. ................. 604/528 |
| 2008/0140079 A1 | 6/2008 | Osorio et al. |
| 2008/0188854 A1 | 8/2008 | Moser |
| 2008/0188928 A1 | 8/2008 | Salahieh et al. |
| 2008/0200915 A1 | 8/2008 | Globerman et al. |
| 2008/0208255 A1 | 8/2008 | Siegal |
| 2008/0228192 A1 | 9/2008 | Beyar et al. |
| 2008/0228195 A1 | 9/2008 | von Jako et al. |
| 2008/0269766 A1 | 10/2008 | Justis |
| 2008/0269796 A1 | 10/2008 | Reiley et al. |
| 2008/0287741 A1 * | 11/2008 | Ostrovsky et al. ............ 600/141 |
| 2009/0069850 A1 | 3/2009 | Fuerderer |
| 2009/0076511 A1 | 3/2009 | Osman |
| 2009/0076517 A1 | 3/2009 | Reiley et al. |
| 2009/0131850 A1 | 5/2009 | Geiger |
| 2009/0131886 A1 | 5/2009 | Liu et al. |
| 2009/0131945 A1 | 5/2009 | Liu et al. |
| 2009/0131948 A1 | 5/2009 | Liu et al. |
| 2009/0156995 A1 * | 6/2009 | Martin et al. ............... 604/95.04 |
| 2009/0157060 A1 | 6/2009 | Teague et al. |
| 2009/0292289 A9 | 11/2009 | Sand et al. |
| 2009/0299282 A1 | 12/2009 | Lau et al. |
| 2010/0010298 A1 | 1/2010 | Bakos et al. |
| 2010/0010299 A1 * | 1/2010 | Bakos et al. .................. 600/108 |
| 2010/0036202 A1 * | 2/2010 | Lin et al. ....................... 600/146 |
| 2010/0057087 A1 * | 3/2010 | Cha ................................. 606/80 |
| 2010/0094029 A1 | 4/2010 | Pellegrino et al. |
| 2010/0121336 A1 | 5/2010 | Linderman et al. |
| 2010/0160923 A1 | 6/2010 | Sand et al. |
| 2010/0241123 A1 | 9/2010 | Middleton et al. |
| 2012/0095517 A1 | 4/2012 | Muller et al. |
| 2012/0130381 A1 | 5/2012 | Germain |
| 2012/0226301 A1 | 9/2012 | Geist |
| 2013/0274784 A1 | 10/2013 | Lenker et al. |

FOREIGN PATENT DOCUMENTS

| | | |
|---|---|---|
| WO | 98/17190 | 4/1998 |
| WO | 98/56299 | 12/1998 |
| WO | 99/49819 | 10/1999 |
| WO | 00/33909 | 6/2000 |
| WO | 02/03870 | 1/2002 |
| WO | 2005/051212 | 6/2005 |
| WO | 2006/050445 | 5/2006 |
| WO | 2007/036815 | 4/2007 |
| WO | 2007/147591 | 12/2007 |
| WO | 2008/011262 | 1/2008 |
| WO | 2010/008818 | 1/2010 |
| WO | 2012/151396 | 11/2012 |

* cited by examiner

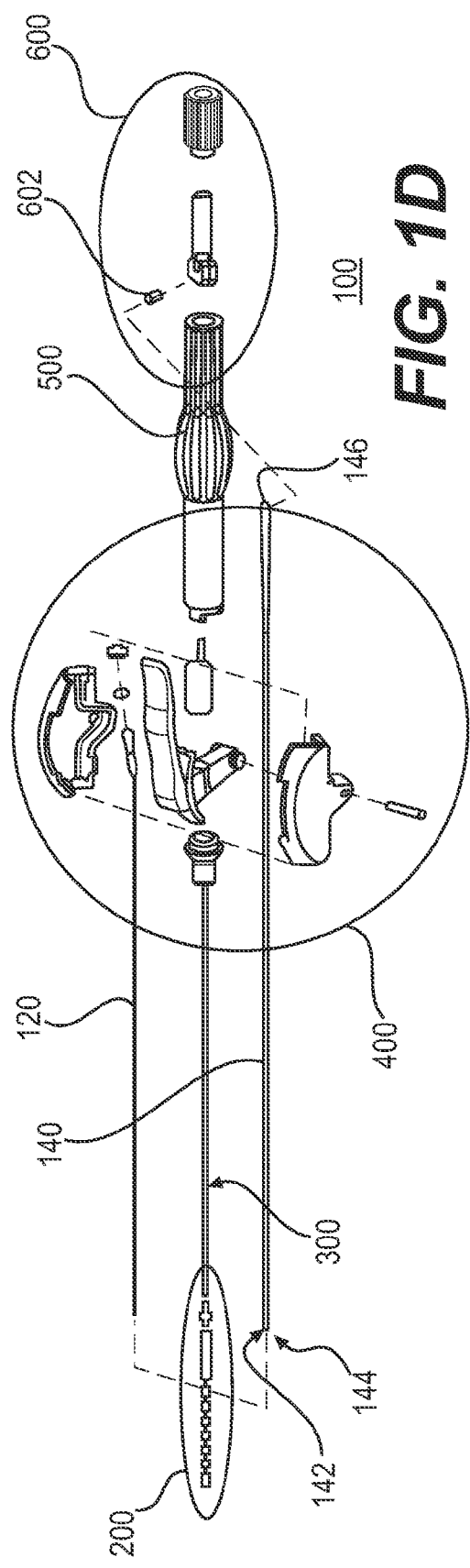
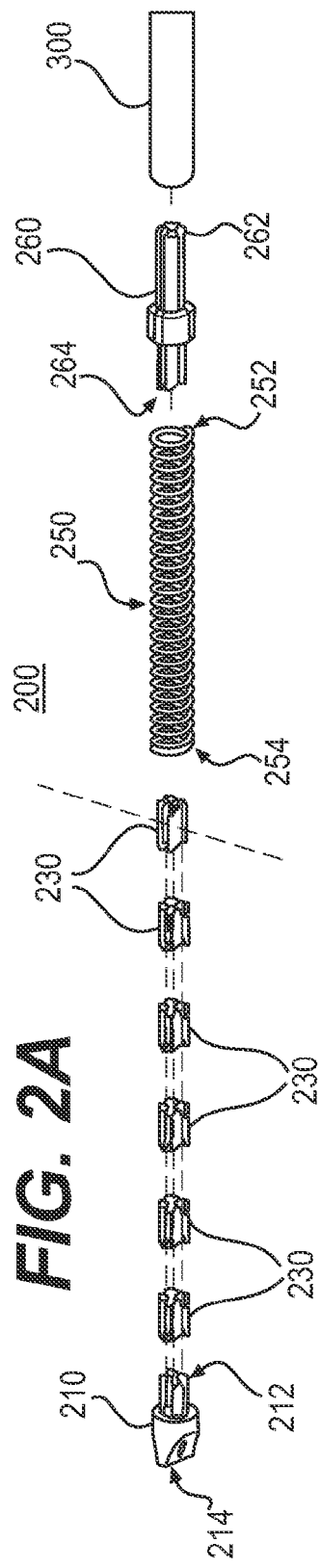
FIG. 1D
FIG. 2A

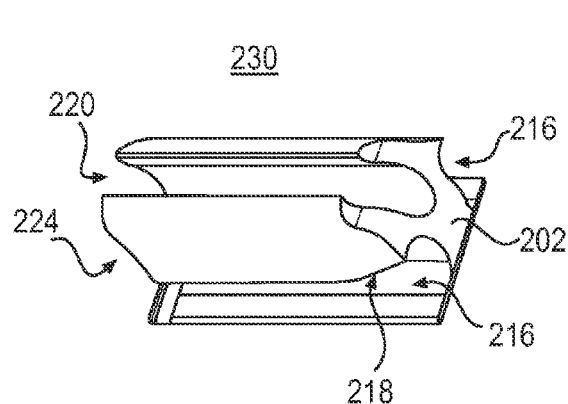
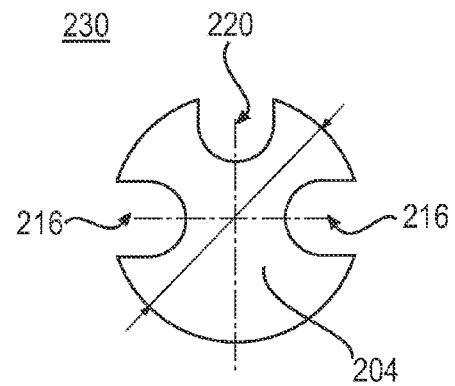
*FIG. 4A*  *FIG. 4B*
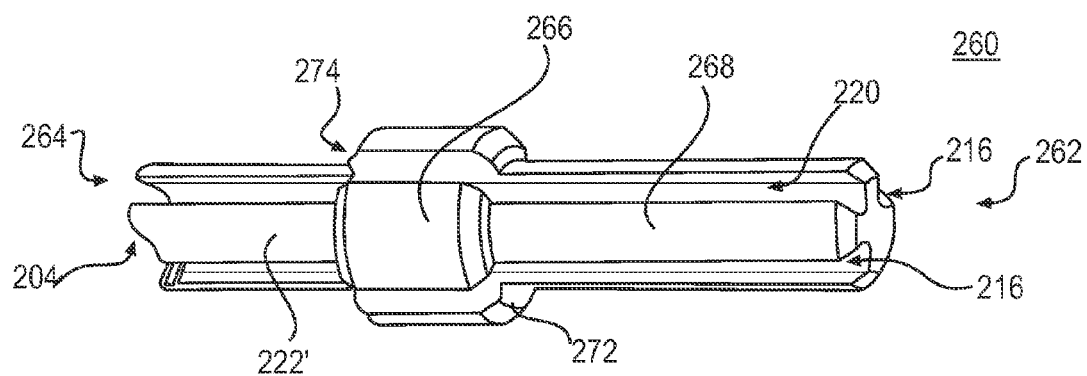
*FIG. 5A*
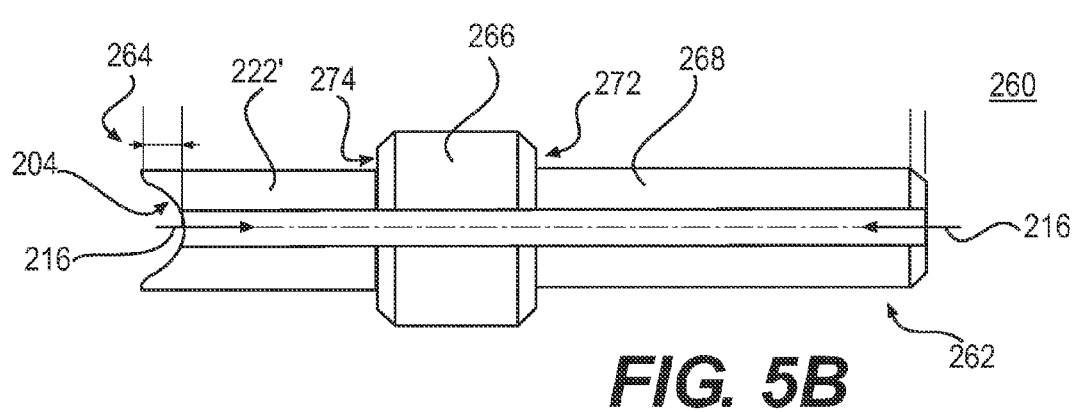
*FIG. 5B*

ARTICULATED CAVITY CREATOR

BACKGROUND

Certain diagnostic or therapeutic procedures require the formation of a cavity in an interior body region. These cavity-forming procedures can be used to treat cortical bone which due to osteoporosis, avascular necrosis, cancer, or trauma, for example, may be fractured or prone to compression fracture or collapse and which, if not successfully treated, can lead to deformities, chronic complications, and an overall adverse impact upon the quality of life for the patient.

Vertebroplasty is where a medical-grade bone cement (such as polymethylmethacrylate, a.k.a., PMMA) is injected percutaneously via a catheter into a fractured vertebra. In this procedure, the bone cement is injected with enough pressure to enable the cement to compress and displace cancellous bone tissue. However, the direction and containment of the injected cement can be difficult to control since the space the bone cement will ultimately occupy is ill-defined, self-forming, and highly-dependent upon the internal composition of the cancellous bone in the vicinity of the injection.

To provide better bounding and control over injected bone cement, other procedures utilize devices for first forming cavities within the cancellous bone (and, accordingly, other interior body regions) prior to injecting bone cement into such a cavity. For example, some devices may utilize an expandable body or balloon that is deployed into the interior body region to form a cavity in, for example, cancellous bone tissue. These expandable body devices effectively compress and displace the cancellous bone to form an interior cavity that then receives a filling material intended to provide renewed interior structural support for cortical bone. However, the effectiveness of expandable or inflatable devices can still be negatively impacted by the internal composition of the cancellous bone in the vicinity of their use—unbeknownst to the surgeon performing the procedure because of a lack of tactile feedback—and removing the expandable or inflatable device may be difficult in certain applications of such processes.

SUMMARY

Various embodiments disclosed herein pertain to devices to create cavities within interior body regions. When deployed though a cannula emplaced into cancellous bone, for example, the distal end of the device can be extended beyond the distal end of the catheter and then be selectively curved into various shaped compression surfaces that, when rotated about a longitudinal axis, creates a void within the interior body. This extended compression surface can then be withdrawn back into the cannula for complete removal from the cannula, and a void filler such as bone cement may then be introduced into the void. For certain embodiments, this bone cement may be introduced through the same cannula used by the cavity creation device.

More specifically, certain embodiments disclosed herein are directed to an articulated tip assembly for creating a cavity in a body, the articulated tip assembly comprising a coil enclosure having a proximal end and a distal end (the coil enclosure being curvable), a shaft coupler coupled to the proximal end of the coil enclosure, a plurality of interconnecting curving elements enclosed within the coil enclosure and movably coupled to the shaft coupler, and a tip coupled to the distal end of the coil enclosure and coupled to the plurality of interconnecting curving elements.

Other implementations are directed to a device for creating a cavity in an interior body, the device comprising an articulated tip assembly, a shaft coupled to the articulated tip assembly, a lever assembly coupled to the shaft, and an off-center cable coupled to the articulated tip assembly and the lever assembly such that variable action of the lever assembly causes the articulated tip assembly to selectively curve, wherein rotation of the device causes the articulated tip assembly to rotate within the interior body. Yet other embodiments are directed to methods for creating a cavity in a target body using an articulated cavity creator, the method comprising inserting an articulated tip assembly into the target body, curving and rotating the articulated tip assembly, and then withdrawing the articulated tip assembly.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein:

FIG. 1D is a exploded perspective view of the articulated cavity creator of FIGS. 1A, 1B, and 1C;

FIG. 2A is an exploded perspective view of an exemplary tip assembly comprising the distal end of an articulated cavity creator representative of several embodiments disclosed herein;

FIG. 4A is a perspective view of a cavity creator curving element representative of various embodiments disclosed herein;

FIG. 4B is a distal end view of the cavity creator curving element of FIG. 4A;

FIG. 5A is a perspective view of a cavity creator shaft coupler representative of various embodiments disclosed herein;

FIG. 5B is a side view of the cavity creator shaft coupler of FIG. 5A;

DETAILED DESCRIPTION

Figure 1A:
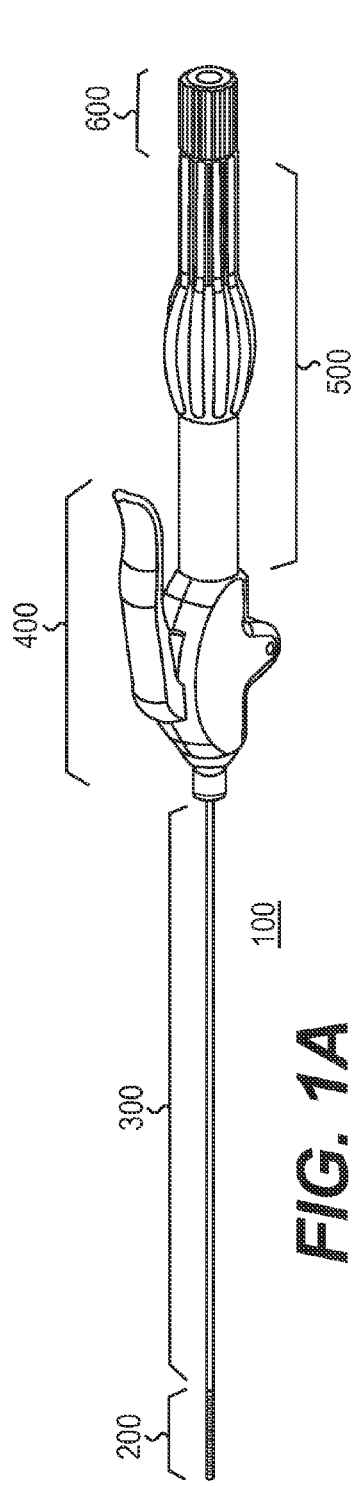
FIG. 1A is a perspective view of an articulated cavity creator representative of various embodiments disclosed herein.

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In addition, various components may be described herein as extending horizontally along a longitudinal direction "L" and lateral direction "A", and vertically along a transverse direction "T". Unless otherwise specified herein, the terms "lateral", "longitudinal", and "transverse" are used to describe the orthogonal directional components of various items. It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the components merely for the purposes of clarity and illustration and are not meant to be limiting.

Figure 1B:
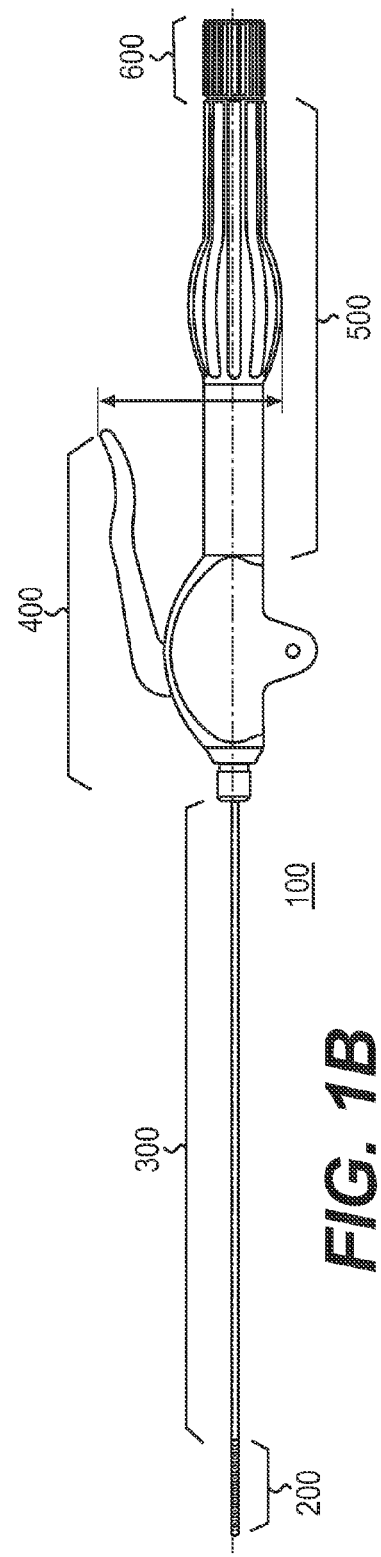
FIG. 1B is a side view of the articulated cavity creator of FIG. 1A.
Figure 1C:
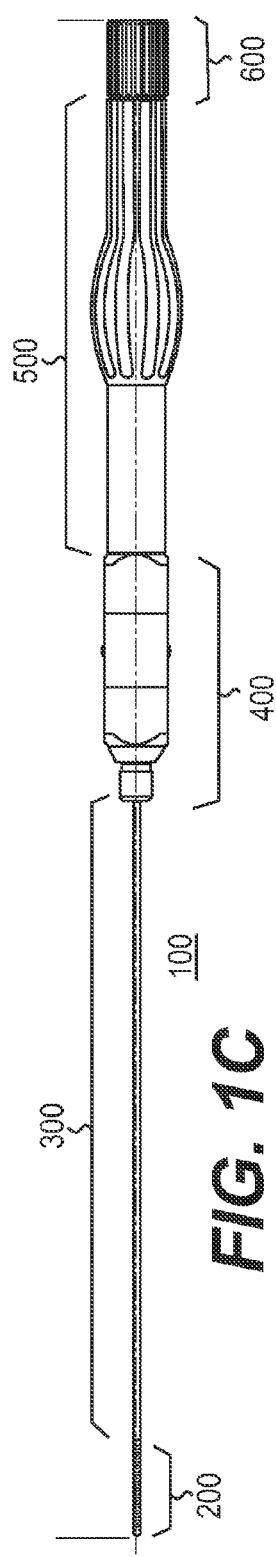
FIG. 1C is a bottom view of the articulated cavity creator of FIGS. 1A and 1B.

FIG. 1A is a perspective view of an articulated cavity creator 100 representative of various embodiments disclosed herein. FIG. 1B is a side view of the articulated cavity creator 100 of FIG. 1A. FIG. 1C is a bottom view of the articulated cavity creator 100 of FIGS. 1A and 1B. FIG. 1D is a exploded perspective view of the articulated cavity creator 100 of FIGS. 1A, 1B, and 1C.

Referring to FIGS. 1A, 1B, 1C, and 1D (collectively referred to herein as "FIG. 1"), an articulated cavity creator ("ACC") may comprise a tip assembly 200, an intra-catheter shaft 300, a lever assembly 400, a rotation shaft 500, and a tensioner assembly 600, each operatively coupled in order from distal end to proximal end of the ACC as shown in FIG. 1. The ACC further comprises an off-center cable 120 and a midline cable 140. The off-center cable 120 is fixedly coupled to the lever assembly 400 at its proximal end, passes longitudinally through the intra-catheter shaft 300, and is fixedly coupled to the tip assembly 200 at its distal end. The midline cable 140, in contrast, is effectively doubled-backed on itself with both ends 142 and 144 fixedly coupled to the tip assembly 200 and passing longitudinally through the intra-catheter shaft 300, the lever assembly 400, the rotation shaft 500, and operationally coupling a rotational component 602 of the tensioner assembly 600 at its bend 146. Each of these components and theirs functions are described in greater detail herein.

Figure 2B:
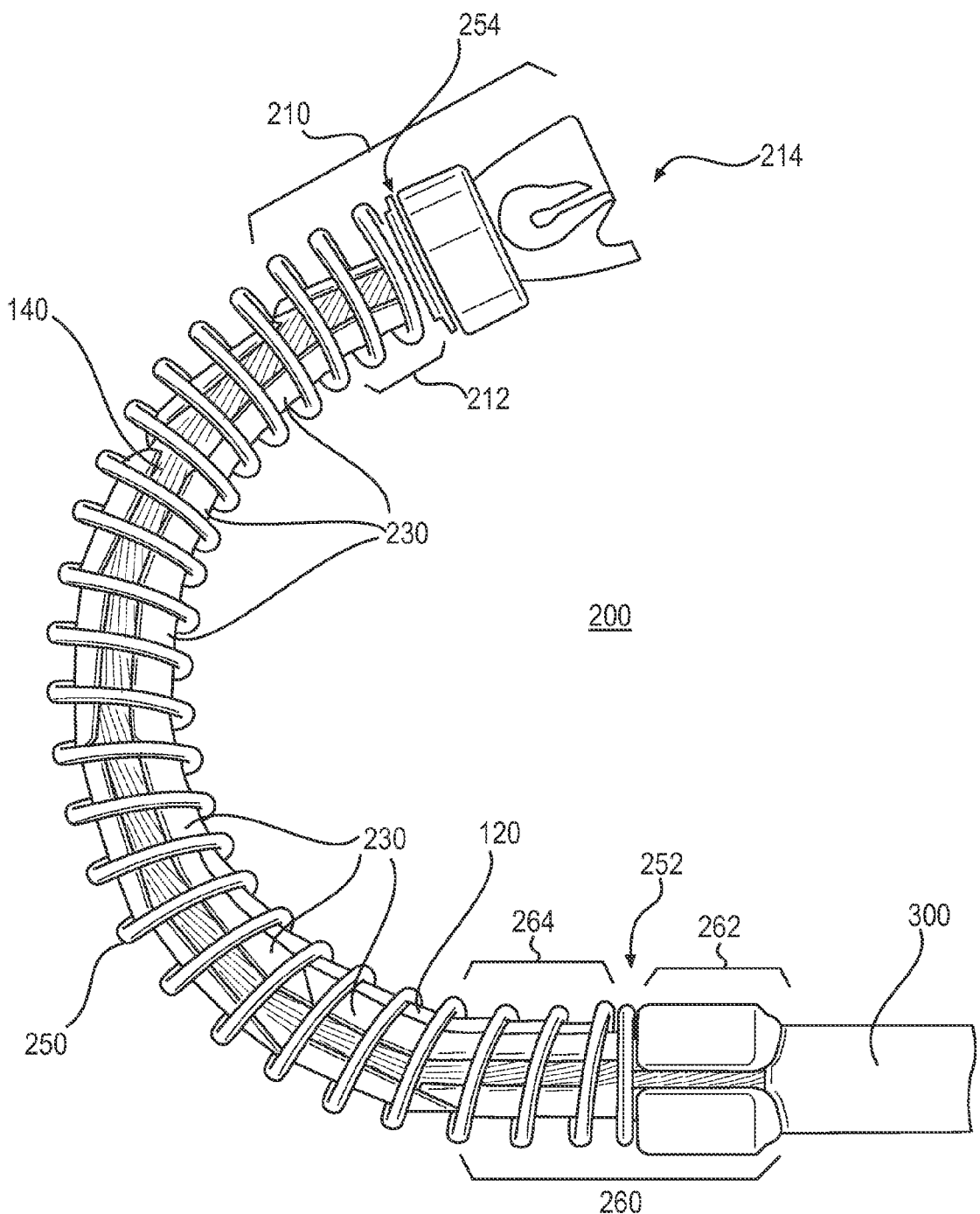
FIG. 2B is a side view of the exemplary tip assembly of FIG. 2A in a curved configuration.

FIG. 2A is an exploded perspective view of an exemplary tip assembly 200 comprising the distal end of an articulated cavity creator 100 representative of several embodiments disclosed herein. FIG. 2B is a side view of the exemplary tip assembly 200 of FIG. 2A in a curved configuration.

Referring to FIGS. 2A and 2B (collectively referred to herein as "FIG. 2"), the tip assembly 200 may comprise a cavity creator tip 210, a plurality of interconnecting curving elements 230, a coil enclosure 250, and shaft coupler 260 for coupling to the intra-catheter shaft 300. As shown in FIG. 2B, the proximal end 212 of the tip 210, the curving elements 230, and the distal end 264 of the shaft coupler 260 are movably coupled and enclosed within the hollow created by the coil enclosure 250, thereby exposing the distal end 214 of the tip 210 beyond the distal end 254 of the coil enclosure 250, as well as exposing the proximal end 262 of the shaft coupler 260 beyond the proximal end 252 of the coil enclosure 250. Moreover, in several alternative embodiments the coil enclosure 250 may be replaced with other enclosures such as a sheath or a series of rings, for example, and that such alternative enclosures may be constructed of any of several suitable materials, including but not limited to rubber, latex, plastic or nitinol.

Further shown in FIG. 2B is the distal end of the doubled-back midline cable 140 running on both sides of the tip assembly 200 (one strand shown, the other strand behind and obstructed from view), both ends of which are fixedly coupled to the tip 210 and run down concurrent lateral channels (highlighted in other illustrations) on each side of the tip 210, the curving elements 230, and the shaft coupler 260, and thereby pass through the hollow of the coil enclosure 250 and through the intra-catheter shaft 300. This midline cable 140 provides the tension necessary to hold the tip 210, the curving elements 230, and the shaft coupler 260 movably coupled and enclosed within the hollow created by the coil enclosure 250. Through the application of even tension by both strands of the midline cable 140, curving of the tip assembly 200 in a vertical (up-and-down) direction is achievable as disclosed herein.

Also shown in FIG. 2B is the distal end of the off-center cable 120 fixedly coupled to the tip 210 and running down a top channel (highlighted in other illustrations) of the tip 210, the curving elements 230, and the shaft coupler 260, and thereby passing through the hollow of the coil enclosure 250 and the intra-catheter shaft 300. This off-center cable 120 provides variable tension on the top side of the tip assembly 200 causing the tip 210, the curving elements 230, and the shaft coupler 260 to together movably curve against the coil enclosure 250 (as shown) in various curved configurations depending on the amount of variable tension applied by the off-center cable 120. As such, the curving elements 230 within tip assembly 200 cooperate to approximate a curved shape. Further, the tip assembly 200 may form such a curved shape around any object that the tip assembly 200 encounters as the off-center cable 120 is tensed along the top side of the tip assembly 200.

The aforementioned curvable motions and restrictions of the tip assembly 200 are further complimented by the shaping of the proximal end 212 of the tip 210, both ends of the curving elements 230, and the distal end 264 of the shaft coupler 260, which help assist curving of the tip assembly 200 in a vertical direction and help prevent curving in a horizontal direction. This shaping is discussed in greater detail later herein.

Figure 3A:
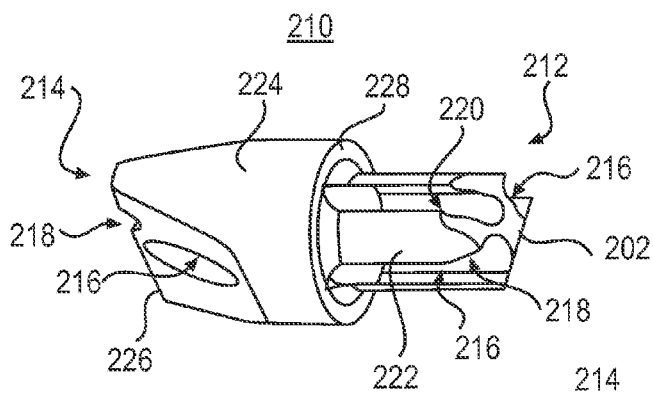
FIG. 3A is a perspective view of a cavity creator tip representative of various embodiments disclosed herein.
Figure 3C:
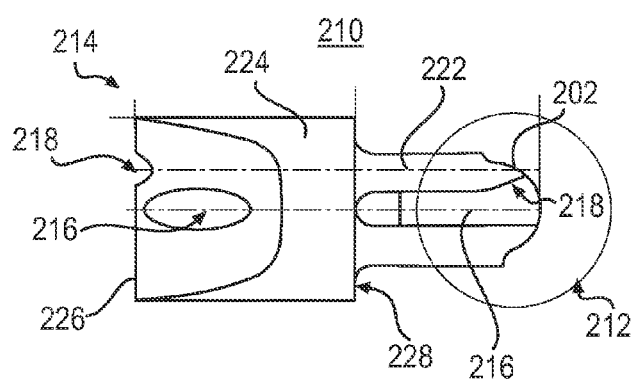
FIG. 3C is a side view of the cavity creator tip of FIGS. 3A and 3B.
Figure 3B:
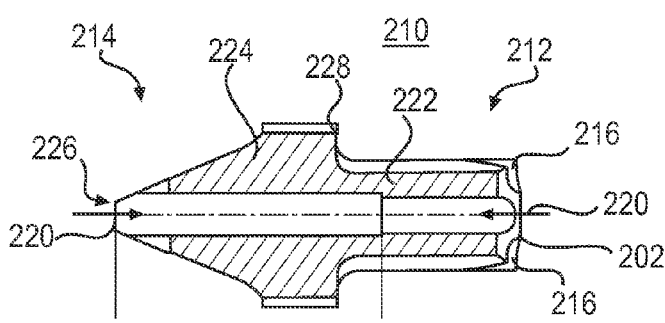
FIG. 3B is a cross-sectional top view of the cavity creator tip of FIG. 3A.
Figure 3D:
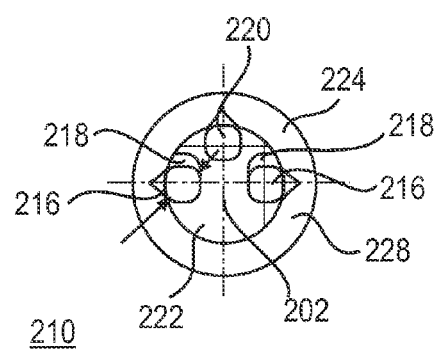
FIG. 3D is a proximal end view of the cavity creator tip of FIGS. 3A, 3B, and 3C.

FIG. 3A is a perspective view of a cavity creator tip 210 representative of various embodiments disclosed herein. FIG. 3B is a cross-sectional top view of the cavity creator tip 210 of FIG. 3A. FIG. 3C is a side view of the cavity creator tip 210 of FIGS. 3A and 3B. FIG. 3D is a proximal end view of the cavity creator tip 210 of FIGS. 3A, 3B, and 3C.

Referring to FIGS. 3A, 3B, 3C, and 3D (collectively referred to herein as "FIG. 3"), the cavity creator tip 210 (or simply "tip") comprises a partial curving element 222 corresponding to the proximal end 212 and a head 224 corresponding to the distal end 214. The partial curving element 222 further comprises two lateral channels 216, one oriented to each side of the tip 210, as well as a top channel 220 oriented to the top of the tip 210. These channels 216 and 220 proceed through the head 224 to open at the distal end of the tip 210 as shown in the illustrations, and for certain embodiments these distal endpoints for the channels 216 and 220 at the head 224 may comprise fastening or welding points for fixedly coupling the both ends 142 of the doubled-back midline cable 140, as well as the distal end of the off-center cable 120, to the tip 210. The head 224 may also comprise a distal edge 226 that is vertically flat (as shown) or, in other embodiments, may be formed to provide a rounded edge or an edge of some other form or shape. The head also comprises a stop surface 228 for engaging but not passing into the distal end of the coil enclosure 250.

The partial curving element 222, insertable into the distal end of the coil enclosure 250, further comprises a partially-cylindrical convex proximal male end 202 for operatively coupling to a corresponding partially-cylindrical distal female end of a curving element 230 to facilitate curving of the tip assembly 200 in a vertical direction and help prevent curving in a horizontal direction (the partially-cylindrical shape being curved in the vertical direction but flat in the horizontal direction). Similarly, the two lateral channels 216 each comprise a slope surface 218 to allow curving of a tip assembly 200 in a vertical "up" direction (but not in a vertical "down" direction) against each strand of the midline cable 140 running through said lateral channels 216.

FIG. 4A is a perspective view of a cavity creator curving element 230 representative of various embodiments disclosed herein. FIG. 4B is a distal end view of the cavity creator curving element 230 of FIG. 4A.

Referring to FIGS. 4A and 4B (collectively referred to herein as "FIG. 4"), each such curving element 230 comprises two lateral channels 216, one oriented to each side of the curving element 230, as well as a top channel 220 oriented to the top of the curving element 230. The curving element 222 further comprises a partially-cylindrical convex proximal male end 202 and a partially-cylindrical concave proximal female end 204. The proximal male end 202 is shaped to operatively couple with the corresponding distal female end 204 of either another curving element 230 or shaft coupler 260. Conversely, the distal female end 204 is shaped to operatively couple with the corresponding proximal male end 202 of either another curving element 230 or the distal end 212 of the tip 210 accordingly.

Both the proximal male end 202 and the distal female end 204 of the curving element 230 facilitate curving of the tip assembly 200 in a vertical direction and help prevent curving in a horizontal direction (the partially-cylindrical shape being curved in the vertical direction but flat in the horizontal direction). Similarly, the two lateral channels 216 each comprise a slope surface 218 to allow curving of a tip assembly 200 in a vertical "up" direction (but not in a vertical "down" direction) against each strand of the midline cable 140 running through said lateral channels 216.

FIG. 5A is a perspective view of a cavity creator shaft coupler 260 representative of various embodiments disclosed herein. FIG. 5B is a side view of the cavity creator shaft coupler 260 of FIG. 5A.

Referring to FIGS. 5A and 5B (collectively referred to herein as "FIG. 5"), the shaft coupler 260 comprises a partial curving element 222' corresponding to the distal end 262, a collar 266 centrally located, and an insertion component 268 corresponding to the proximal end 264. The shaft coupler 260 further comprises two lateral channels 216, one oriented to each side of the shaft coupler 260, as well as a top channel 220 oriented to the top of the shaft coupler 260, where all three channels run from the proximal end 262 to the distal end 264 of the shaft coupler 260.

The partial curving element 222', insertable into the proximal end of the coil enclosure 250, further comprises a partially-cylindrical concave distal female end 204 for operatively coupling to a corresponding partially-cylindrical proximal male end 202 of a curving element 230 to facilitate curving of the tip assembly 200 in a vertical direction and help prevent curving in a horizontal direction (the partially-cylindrical shape being curved in the vertical direction but flat in the horizontal direction). The collar 266 comprises a first stop surface 272 for engaging but not passing into the distal end of the intra-catheter shaft 300, as well as a second stop surface 274 for engaging but not passing into the proximal end of the coil enclosure 250. The insertion component 268, in turn, is insertable into the distal end of the intra-catheter shaft 300 and, for certain embodiments, may be fastening or welded to said intra-catheter shaft 300.

Figure 6:
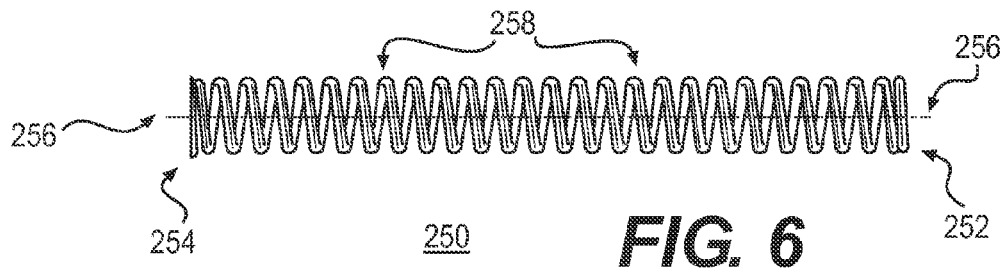
FIG. 6 is a side view of a cavity creator coil enclosure representative of various embodiments disclosed herein.

FIG. 6 is a side view of a cavity creator coil enclosure 250 representative of various embodiments disclosed herein. The coil enclosure 250 is both compressible relative to the longitudinal direction as shown, as well as curvable relative from the longitudinal direction as shown. The proximal end 252 of the coil enclosure 250 operatively couples with the second stop surface 274 of the shaft coupler 260, and the distal end 254 of the coil enclosure 250 operatively couples with the stop surface 228 of the tip 210. The helical body 258 of the coil enclosure 250 forms a hollow 256 extending from the distal end 254 to the proximal end 252 of the coil enclosure 250 and effectively encloses the proximal end 212 of the tip 210, the plurality of interconnecting curving elements 230, and the distal end 264 of the shaft coupler 260 that comprise the tip assembly 200. The tip assembly 200, in turn, couples to the distal end of the intra-catheter shaft 300, and the midline cable 140 and the off-center cable 120 fixedly coupled to the tip 210 pass through the tip assembly 200 and through the intra-catheter shaft 300 to the lever assembly 400 in the case of the off-center cable 120, and through the lever assembly 400 and the rotation shaft 500 to the tensioner assembly 600 in the case of both strands of the midline cable 140.

Figure 7A:
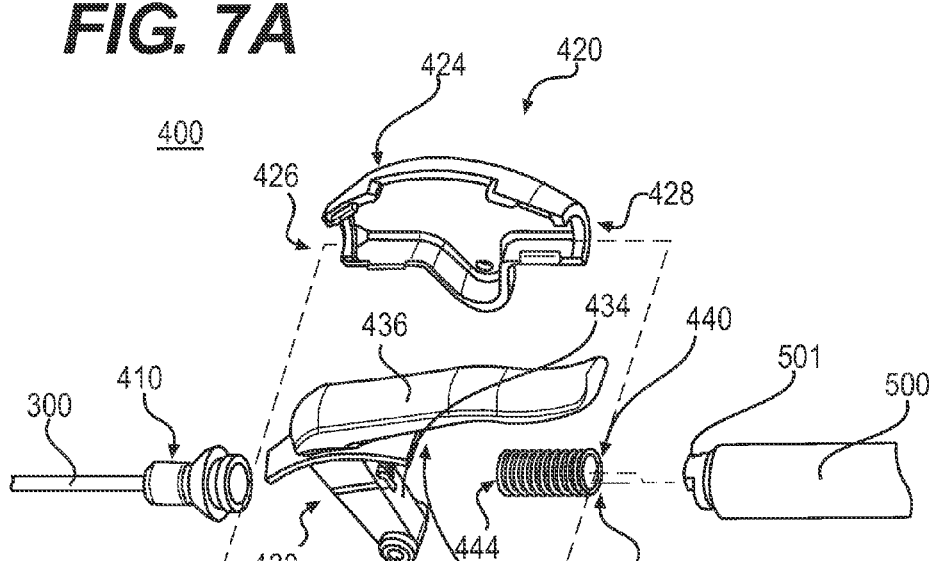
FIG. 7A is an exploded perspective view of an exemplary lever assembly of an articulated cavity creator representative of several embodiments disclosed herein.
Figure 7B:
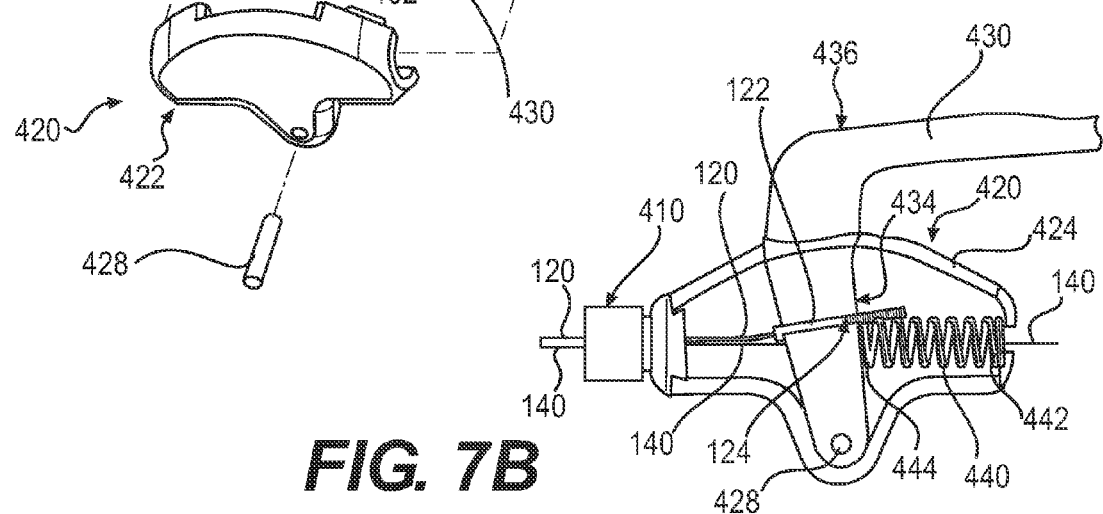
FIG. 7B is an exposed side view of the exemplary lever assembly of FIG. 7A.

FIG. 7A is an exploded perspective view of an exemplary lever assembly 400 of an articulated cavity creator 100 representative of several embodiments disclosed herein. FIG. 7B is an exposed side view of the exemplary lever assembly 400 of FIG. 7A (with the left body 422 of the lever pivot 420 removed).

Referring to FIGS. 7A and 7B (collectively referred to herein as "FIG. 7"), the lever assembly 400 comprises a receiver 410, a lever pivot 420 (comprising a left body 422 and a right body 424) a lever 430, and a lever spring 440. Also shown for reference are the proximal end of the intra-catheter shaft 300 and the distal end of the rotation shaft 500.

The distal end of the receiver 410 is coupled to the intra-catheter shaft 300, while the proximal end of the receiver 410 is coupled to the distal end 448 of the lever pivot 420. The lever pivot 420 is also movably coupled to the lever 430 via a pivot pin 428 where the pivot pin 428 is coupled at each end to the left body 422 and right body 424 of the lever pivot 420 and passes through the pivot channel 432 of the lever 430 to couple with the lever 430. In various embodiments, pivot pin 428 may be fixedly coupled to the lever pivot 420, the lever 430, or neither (i.e., movably coupled to both). The lever spring 440 comprises a proximal end 442 operatively coupled to a boss 501 of the rotation shaft 500, and a distal end 444 operatively coupled to a proximal surface 434 of the lever 430.

As further illustrated in FIG. 7B, the midline cable 140 (one strand visible and the other strand obscured behind the visible strand) passes through the receiver 410, the lever 430, and the lever spring 440. The off-center cable 120 passes through the receiver 410 and is fixedly connected to the lever 430. In certain embodiments, as illustrated, the off-center cable 120 may be fixedly attached to a threaded coupling rod 122 that then screws through a channel 438 in the lever 430 and is affixed in position with a washer and nut combination 124.

The lever spring 440 exerts pressure against the lever 430 to maintain the lever 430 in a longitudinally forward position (in the distal direction) which, in turn, keeps the tip assembly 200 in an uncurved orientation. However, pressure applied to the pressure surface 436 of the lever 430 causes the lever to pivot longitudinally backward (in the proximal direction) which, in turn, causes the tip assembly 200 to curve about an axis. (The motion of the tip assembly 200 thus carves a narrow path through, for example, cancellous bone.)

Figure 8A:
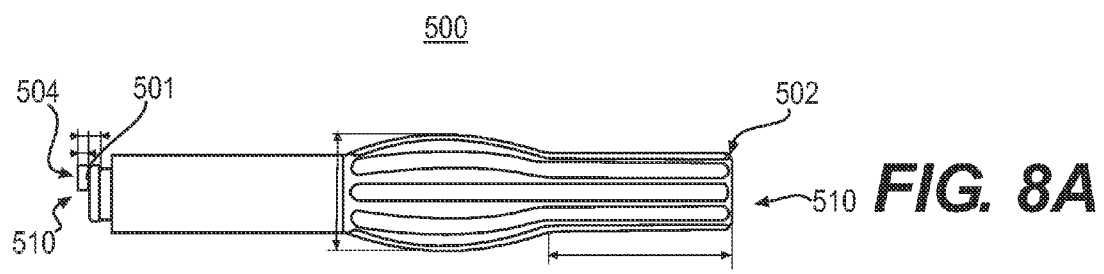
FIG. 8A is side view of an exemplary rotation shaft of an articulated cavity creator representative of several embodiments disclosed herein.
Figure 8B:
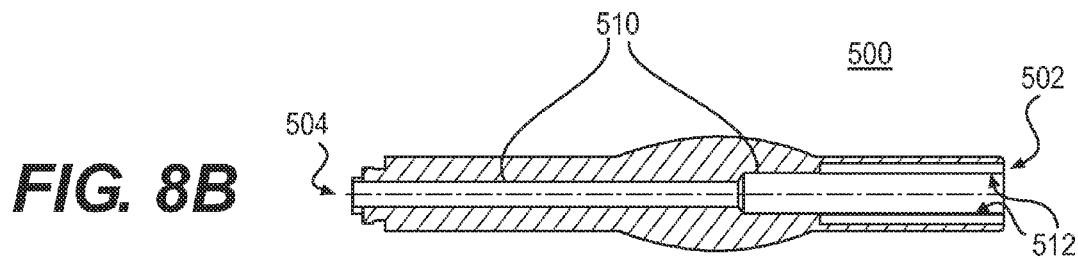
FIG. 8B is a cross-sectional view of the exemplary rotation shaft of FIG. 8A.

FIG. 8A is side view of an exemplary rotation shaft 500 of an articulated cavity creator 100 representative of several embodiments disclosed herein. FIG. 8B is a cross-sectional view of the exemplary rotation shaft 500 of FIG. 8A.

Referring to FIGS. 8A and 8B (collectively referred to herein as "FIG. 8"), the rotation shaft 500 comprises a proximal end 502 for operationally coupling to a tensioner assembly 600 as well as a distal end 504 (e.g., a groove) for fixedly coupling to a lever assembly 400. The rotation shaft 500 also comprises a central channel 510 through which the midline cable 140 passes. The proximal end 502 further comprises two coupling slots 512 to movably couple the tensioner (not shown) of the tensioner assembly 600 (described in more detail below). The rotation shaft 500 enables an operator (such as a surgeon) to rotate (or "twist") the entire articulated cavity creator 100 and, in turn, rotate (or "spin") the tip assembly 200 in a manner that, coupled with the variable curving ability provided by the lever assembly 400, carves out a cavity within, for example, cancellous bone.

Figure 9:
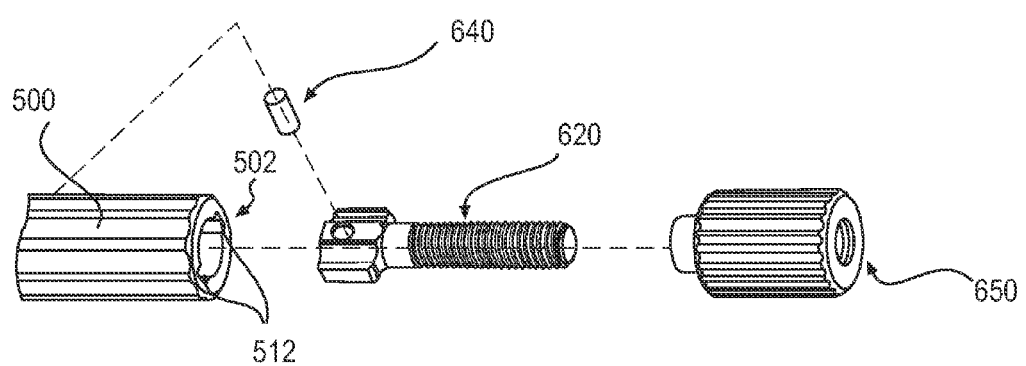
FIG. 9 is an exploded perspective view of an exemplary tensioner assembly comprising the proximal end of an articulated cavity creator representative of several embodiments disclosed herein.

FIG. 9 is an exploded perspective view of an exemplary tensioner assembly 600 comprising the proximal end of an articulated cavity creator 100 representative of several embodiments disclosed herein. As illustrated, the tensioner assembly 600 comprises a tensioner 620, a midline pin 640, and a tension knob 650. Also shown for reference is the proximal end 502 of the rotation shaft 500, said proximal end comprising the two coupling slots 512 to movably couple the tensioner 620.

Figure 10A:
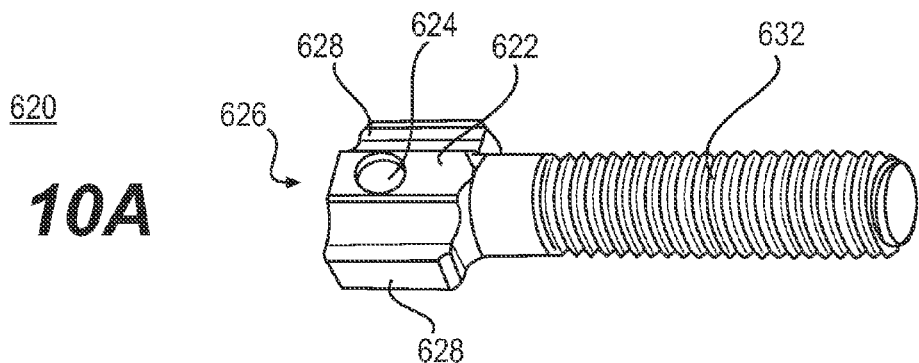
FIG. 10A is a perspective view of a cavity creator tensioner representative of various embodiments disclosed herein.
Figure 10B:
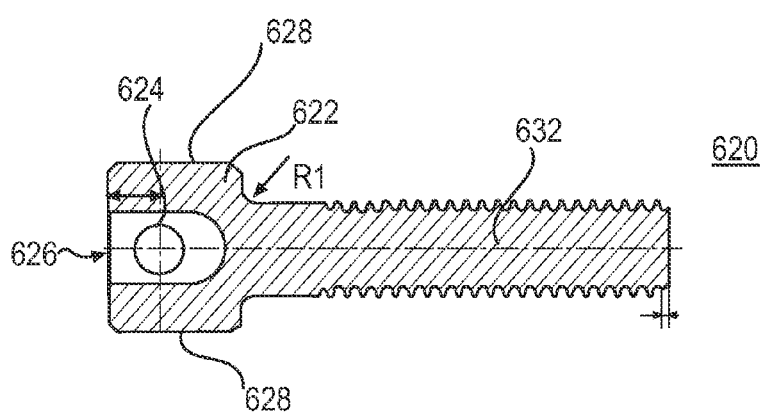
FIG. 10B is a cross-sectional top view of the cavity creator tensioner of FIG. 10A.
Figure 10C:
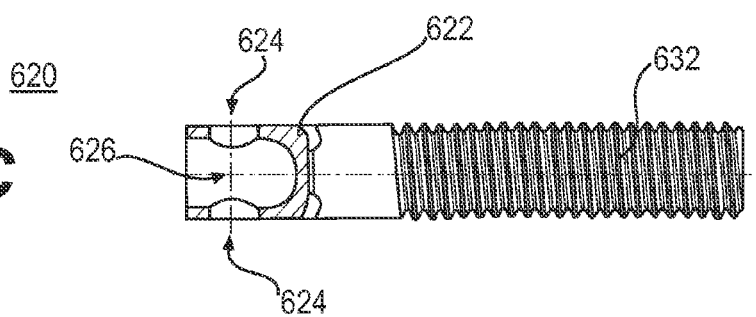
FIG. 10C is a partially-cross-sectional side view of the cavity creator tensioner of FIGS. 10A and 10B.
Figure 10D:
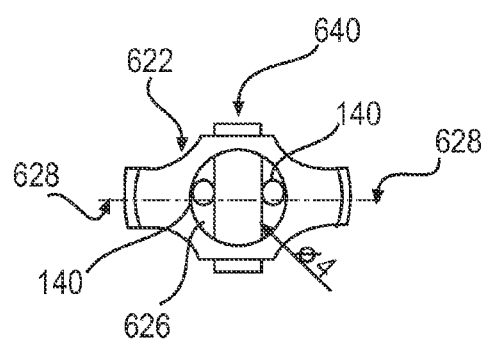
FIG. 10D is a distal end view of the cavity creator tensioner of FIGS. 10A, 10B, and 10C.

FIG. 10A is a perspective view of a cavity creator tensioner 620 representative of various embodiments disclosed herein. FIG. 10B is a cross-sectional top view of the cavity creator tensioner 620 of FIG. 10A. FIG. 10C is a partially-cross-sectional side view of the cavity creator tensioner of FIGS. 10A and 10B. FIG. 10D is a distal end view of the cavity creator tensioner of FIGS. 10A, 10B, and 10C.

Referring to FIGS. 10A, 10B, 10C, and 10D (collectively referred to herein as "FIG. 10"), the tensioner 620 comprises a tension head 622 fixedly coupled to a threaded shaft 632 for engaging the tension knob 650. The tension head 622 further comprises a pin hole 624, a cable return cavity 626, and two slotting edges 628. The two slotting edges 628 slidably engage the two coupling slots 512 of the rotation shaft 500, thus preventing rotation of the tensioner 620 within the rotation shaft 500 while also ensuring that the tensioner perfectly rotates along with the rotation shaft 500 when it is rotated.

In operation, the proximal end of the doubled-back midline cable 140, comprising a 180-degree turn in the cable, is inserted into cable return cavity 626 and the midline pin 640 is introduced through the pin hole 624 to hold the midline cable 140 in place (as shown in FIG. 10D). In this manner, the midline cable 140, being movable along the proximal rounded surface of the midline pin 640, provides even tension throughout the entire device to the tip assembly 200.

Figure 11A:
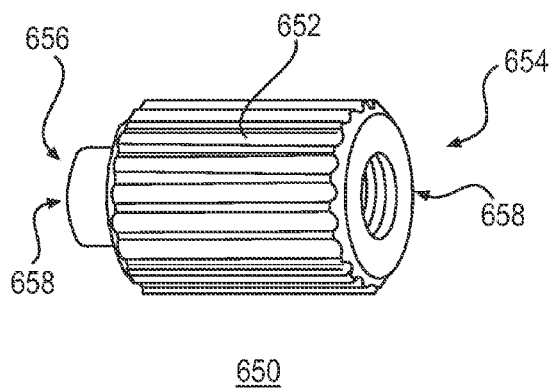
FIG. 11A is a perspective view of a cavity creator tension knob representative of various embodiments disclosed herein.
Figure 11B:
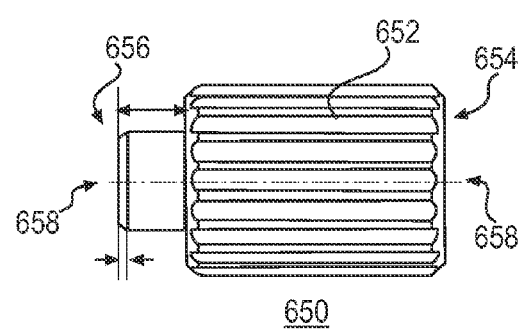
FIG. 11B is a side view of the cavity creator tension knob of FIG. 11A.
Figure 11C:
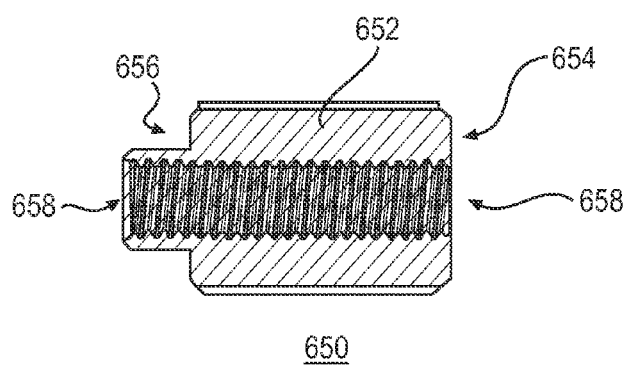
FIG. 11C is a cross-sectional side view of the cavity creator tension knob of FIGS. 11A and 11B.
Figure 11D:
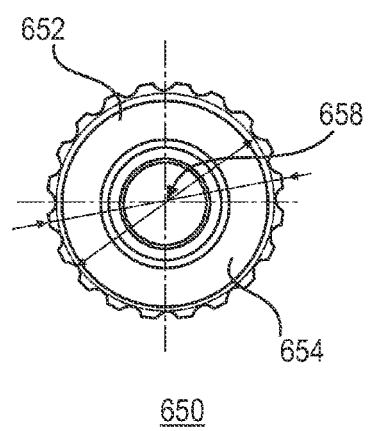
FIG. 11D is a proximal end view of the cavity creator tension knob of FIGS. 11A, 11B, and 11C.

FIG. 11A is a perspective view of a cavity creator tension knob 650 representative of various embodiments disclosed herein. FIG. 11B is a side view of the cavity creator tension knob 650 of FIG. 11A. FIG. 11C is a cross-sectional side view of the cavity creator tension knob 650 of FIGS. 11A and 11B. FIG. 11D is a proximal end view of the cavity creator tension knob 650 of FIGS. 11A, 11B, and 11C.

Referring to FIGS. 11A, 11B, 11C, and 11D (collectively referred to herein as "FIG. 11"), the tension knob 650 comprises a twist body 652 having a proximal end 654 and a distal end 656 and a threaded hole 658 running from the proximal end 654 to the distal end 656. The distal end 656 abuts against the proximal end 502 of the rotation shaft 500 but is still able to rotate. The threaded hole 658 engages the threaded shaft 632 of the tensioner 620 enabling the tension knob 650 to draw the tensioner 620 back in a proximal direction by rotably turning the tension knob 650 in one direction (e.g. clockwise) and thereby increase the tension on the midline wire 140. Conversely, by rotably turning the tension knob 650 in the opposite direction (e.g., counterclockwise), the threaded shaft 632 of the tensioner 620 is pushed forward in the distal direction and decreases tension on the midline wire 140.

Figure 12B:
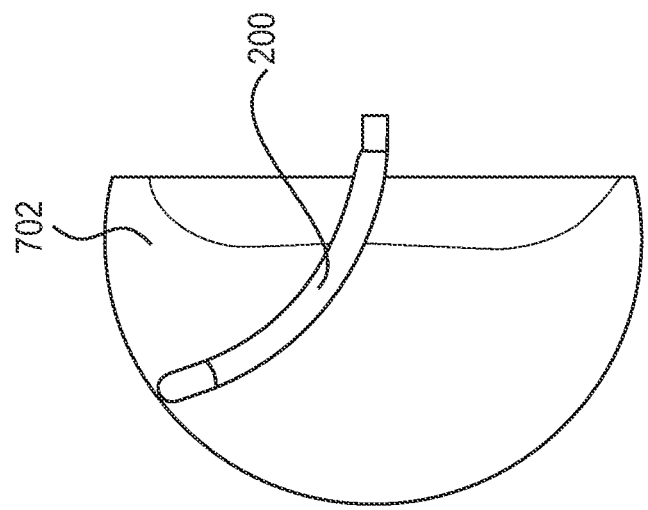
FIG. 12B is a side view of the maximum cavity of FIG. 12A further including the tip assembly of FIG. 2 in position within the interior body.
Figure 12A:
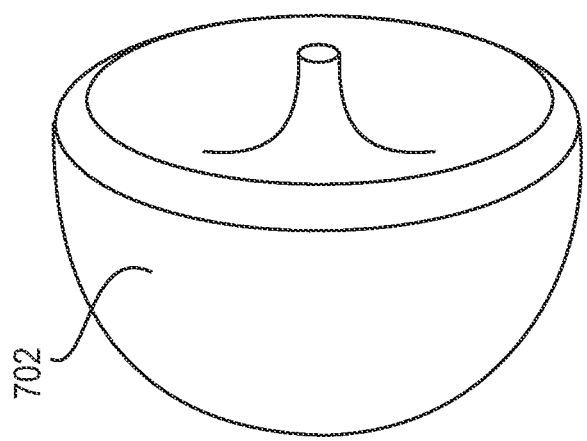
FIG. 12A is a perspective view of a maximum cavity creatable utilizing certain embodiments of the cavity creator disclosed herein.
Figure 12C:
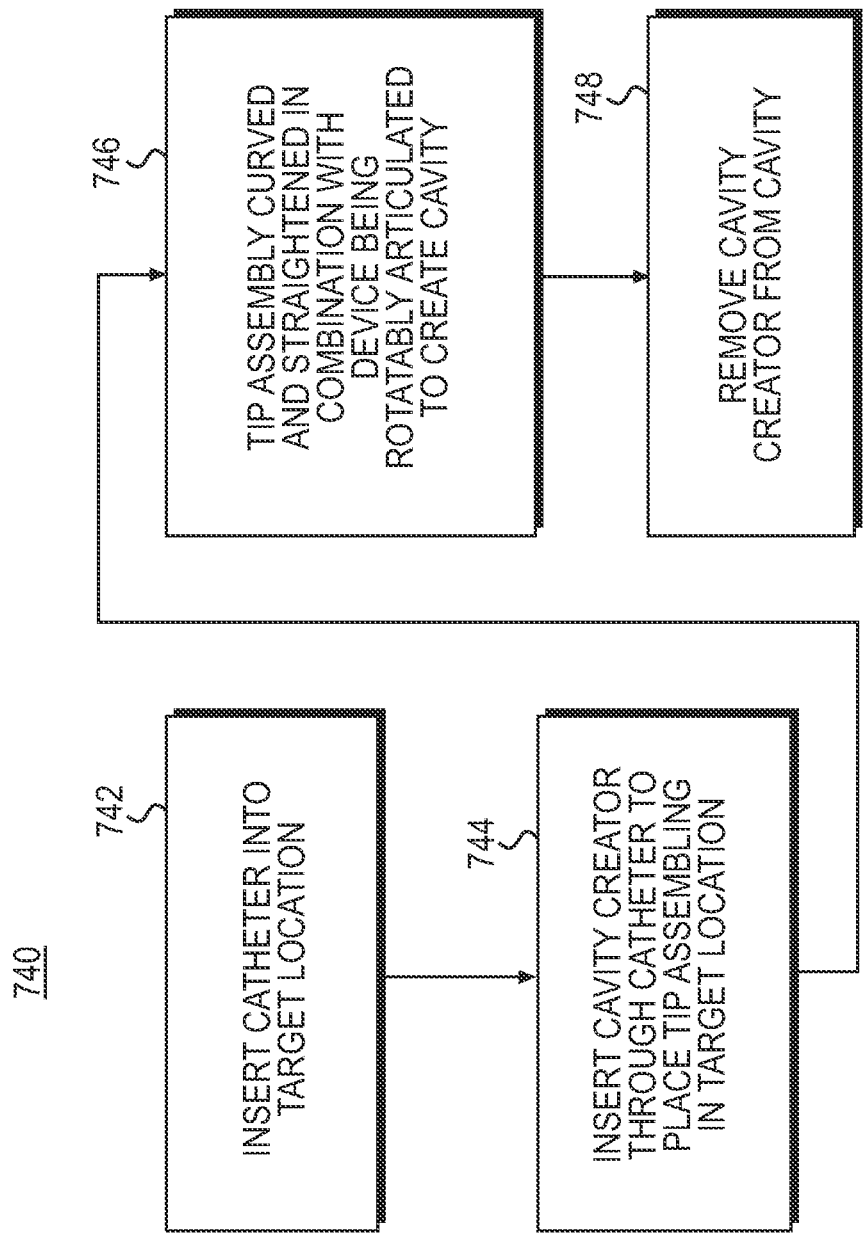
FIG. 12C is an operational flow diagram illustrating a method for creating the cavity illustrated in FIGS. 12A and 12B utilizing certain embodiments of the cavity creator disclosed herein.

FIG. 12A is a perspective view of a maximum cavity 702 creatable utilizing certain embodiments of the articulated cavity creator 100 disclosed herein. FIG. 12B is a side view of the maximum cavity of FIG. 12A further including the tip assembly 200 of FIG. 2 in position within the interior body. FIG. 12C is an operational flow diagram illustrating a method 740 for creating the cavity illustrated in FIGS. 12A and 12B utilizing certain embodiments of the cavity creator disclosed herein.

Referring to FIGS. 12A, 12B, and 12C (collectively referred to herein as "FIG. 12"), the method 740 comprises, at 742, inserting a catheter into a target location such as an interior body (e.g., a region of cancellous bone). At 744, inserting the articulated cavity creator 100 through the catheter such that the tip assembly 100 extends beyond the distal end of the catheter and into the target region. At 746, the tip assembly 200 is curved and straightened by action of the lever 430 in combination with the articulated cavity creator 100 being rotated via the rotation shaft 500. For example, in one approach, the tip assembly 100 might be incrementally curved through its range of motion (from straight to maximally curved), moving the tip 210 no more than its width with each increment, and at each increment rotating the rotation shaft 500 at least a full 360-degrees. In another approach, the rotation shaft might be rotated incrementally through a full rotation (360-degrees), rotating the tip 210 with each increment no more than the tip's 210 width in each increment position (such as when curved perpendicular to the intra-catheter shaft 300), and at each increment engaging the lever 430 to move the tip assembly 200 through its full range of motion from straight to maximally curved and back. At 738, the articulated cavity creator 100 is removed.

It should be noted that specific features of the various embodiments disclosed herein can be performed manually by user-applied forces or, alternately, utilizing specialized motors. For example, the rotation and curving of the device to form a cavity can be performed manually by a surgeon who rotates the device via the rotation shaft and also curves the device by action of the lever assembly. Conversely, the rotation and/or the curving of the tip assembly can be performed by motorized components that may utilize, in certain implementations, microprocessors or other guidance systems to coordinate the rotation and curving motions to optimally form the cavity within the target body.

As will be readily appreciated by those of skill in the art, the various components described herein can be formed from a variety of biocompatible materials, such as cobalt chromium molybdenum (CoCrMo), titanium and titanium alloys, stainless steel or other metals, as well as ceramics or polymers. A coating may be added or applied to the various components described herein to improve physical or chemical properties, such as a plasma-sprayed titanium coating or Hydroxypatite. Moreover, skilled artisans will also appreciate that the various components herein described can be constructed with any dimensions desirable for implantation and cavity creation.

In addition, the various embodiments disclosed herein may be adapted for use in virtually any interior body region where the formation of a cavity within tissue is required for a therapeutic or diagnostic purpose. While several embodiments are herein described with regard to treating bones, other embodiments can be used in other interior body regions as well. In addition, it is also anticipated that certain embodiments could be used for purposes other than medical, such as construction, manufacturing, and excavation, among others; accordingly, nothing herein is intended to limit application of the various embodiments to purely medical uses.

Accordingly, the subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

What is claimed is:

1. An articulated tip assembly for creating a cavity in a body, the articulated tip assembly comprising:
    an enclosure having a proximal end and a distal end, the enclosure adapted to change shape;
    a shaft coupler coupled to the proximal end of the enclosure;
    a plurality of interconnecting curving elements enclosed within the enclosure and movably coupled to the shaft coupler, each of the plurality of interconnecting curving elements includes a first channel;
    a tip having:
    a body portion coupled to the distal end of the enclosure and coupled to the plurality of interconnecting curving elements, a proximal end of the body including a partially-cylindrical convex male portion for operatively coupling with a corresponding partially-cylindrical concave female portion of an adjacent interconnecting curving element;
    a head at a distal end of the body portion, the head defining a diameter greater than a diameter of the body portion, wherein the head continuously tapers from the distal end of the body portion to a distal edge of the head, the distal edge located at an end of the head opposite the distal end of the body portion;
    a first channel extending from the body portion into a bore provided in the head, the bore passing through the head from an opening in the partially-cylindrical convex male portion to an opening in a distal end of the head; and
    a second channel extending from the body into a second bore provided in the head, the second channel including an upper surface, a portion of the upper surface defines a sloped surface extending in a direction away from a centerline of the channel,
    and
    an off-center cable fixedly coupled to the tip and passing through the first channel provided in each of the plurality of interconnecting curving elements and the first channel provided in the body of the tip and into the bore provided in the head of the tip, wherein a force applied to the off-center cable causes the plurality of interconnecting curving elements to approximate a curved shape.

2. The articulated tip assembly of claim 1, wherein the enclosure causes the plurality of interconnecting elements to uncurve in the absence of the force.

3. The articulated tip assembly of claim 2, further comprising an assembly fixedly coupled to the off-center cable for variably applying force to selectively curve the articulated tip assembly.

4. The articulated tip assembly of claim 1, wherein a force applied to the off-center cable straightening wire causes the plurality of interconnecting elements to uncurve.

5. The articulated tip assembly of claim 1, further comprising a midline cable fixedly coupled to the tip and passing through the second channel of the tip and the enclosure,
    wherein tension applied to the midline cable causes the tip and the plurality of interconnecting curving elements to be coupled and enclosed by the enclosure.

6. The articulated tip assembly of claim 5, further comprising a tensioner assembly coupled to the midline cable for variably applying tension to the midline cable.

7. The articulated tip assembly of claim 5, wherein the midline cable is doubled-back forming a first strand and a second strand and a bend,
- wherein each of the plurality of interconnecting curving elements includes a second channel and a third channel,
- wherein the tip includes the second channel and a third channel extending from the body portion into a corresponding second and third bore provided in the head,
- wherein the first strand passes through the second channel provided in each of the plurality of interconnecting curving elements and the second strand passes through the third channel provided in each of the plurality of interconnecting curving elements and into the second and third channels of the head, respectively, and into the second and third bores, respectively,
- wherein both the first strand and the second strand are fixedly coupled to the tip at the second and third bores respectively, and
- wherein the bend extends beyond the proximal end of the enclosure.

8. The articulated tip assembly of claim 7, further comprising a tensioner assembly coupled to the bend of the midline cable for variably applying equal tension to both the first strand and the second strand of the midline cable.

9. The articulated tip assembly of claim 1, wherein each curving element from among the plurality of curving elements further comprise a partially-cylindrical convex male end and a partially-cylindrical female end such that the partially-cylindrical convex male end of a first curving element may movably couple with the partially-cylindrical female end of an adjoining second curving element.

10. The articulated tip assembly of claim 1, further comprising a shaft coupled to the shaft coupler for emplacing the device into the body.

11. The articulated tip assembly of claim 10, wherein the body is an interior body.

12. The articulated tip assembly of claim 11, wherein the articulated tip assembly is introducible into the interior body via a catheter.

13. The articulated tip assembly of claim 11, wherein the interior body is comprised of cancellous bone.

14. The articulated tip assembly of claim 1, wherein the sloped surface extends in a direction away from the centerline of the channel to permit curving of the midline cable in a shape corresponding to the off-center cable.

15. The articulated tip assembly of claim 1, wherein the opening in the partially-cylindrical convex male portion is located a position other than an apex of the partially-cylindrical convex male portion.

* * * * *